United States Patent
Yakkanti et al.

(10) Patent No.: US 12,383,342 B2
(45) Date of Patent: Aug. 12, 2025

(54) PINLESS NAVIGATION SYSTEM

(71) Applicants: Madhusudhan Reddy Yakkanti, Prospect, KY (US); Marshall P. Allegra, Prospect, KY (US)

(72) Inventors: Madhusudhan Reddy Yakkanti, Prospect, KY (US); Marshall P. Allegra, Prospect, KY (US)

(73) Assignees: Ramakanth Reddy Yakkanti, Orlando, FL (US); Paul Rocco Allegra, Edmond, OK (US)

( * ) Notice: Subject to any disclaimer, the term of this patent is extended or adjusted under 35 U.S.C. 154(b) by 455 days.

(21) Appl. No.: 17/945,483

(22) Filed: Sep. 15, 2022

(65) Prior Publication Data
US 2024/0090952 A1    Mar. 21, 2024

Related U.S. Application Data

(60) Provisional application No. 63/245,256, filed on Sep. 17, 2021.

(51) Int. Cl.
*A61B 5/00* (2006.01)
*A61B 34/20* (2016.01)
*A61F 2/46* (2006.01)

(52) U.S. Cl.
CPC ............ *A61B 34/20* (2016.02); *A61F 2/4607* (2013.01); *A61F 2/4609* (2013.01); *A61B 2034/2048* (2016.02); *A61F 2002/4632* (2013.01)

(58) Field of Classification Search
None
See application file for complete search history.

(56) References Cited

U.S. PATENT DOCUMENTS

2012/0157887 A1\* 6/2012 Fanson .................. A61B 34/25
                                                                        600/595

\* cited by examiner

*Primary Examiner* — Joel F Brutus
(74) *Attorney, Agent, or Firm* — Patterson

(57) ABSTRACT

In some embodiments, the systems and corresponding methods for accurate and precise placement of joint replacement implants or to assess bony drilling, reaming or cuts are disclosed. A method for assisting in precise and accurate placements of joint replacement implants during a surgery comprises: receiving, by a pinless navigation system, electronic signals carrying data collected by sensors; wherein the sensors are pinless, are placed on a patient's skin, and generate the data by probing a plurality of locations within a patient's body; based on the data included in the electronic signals received from the sensors, calculating, by the pinless navigation system, angular and distance values, which are between the plurality of locations within the body, for performing a surgery on the patient.

20 Claims, 13 Drawing Sheets

902 Receive, by a pinless navigation system, electronic signals carrying data collected by sensors, which have been placed on a skin of a patient and which generated the data by probing a plurality of locations within a body of the patient 904 Parse, by the pinless navigation system, the received electronic signals to extract, from the electronic signals, the data collected by the sensors and that was obtained, by the sensors, by probing the plurality of locations within the body of the patient 906 Based on, at least in part, the data extracted from the electronic signals, calculating, by the pinless navigation system and for performing a surgery on the patient, angular and distance values of angular and distance relations between the plurality of locations within the body of the patient 908 Additional signals received from the sensors? — YES

NO

910 Stop

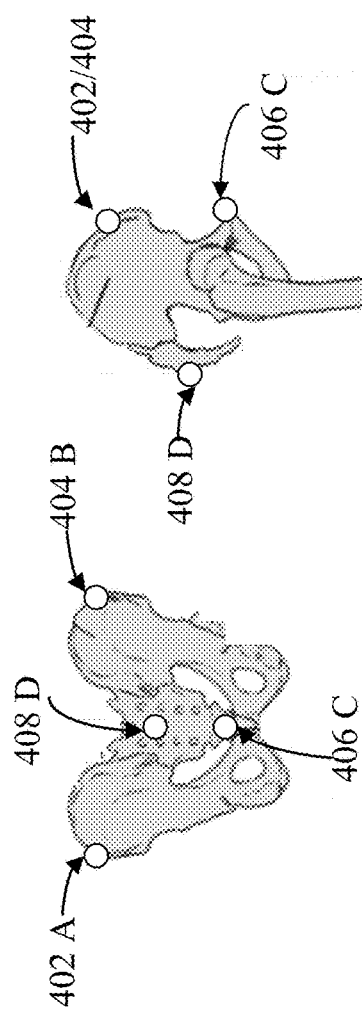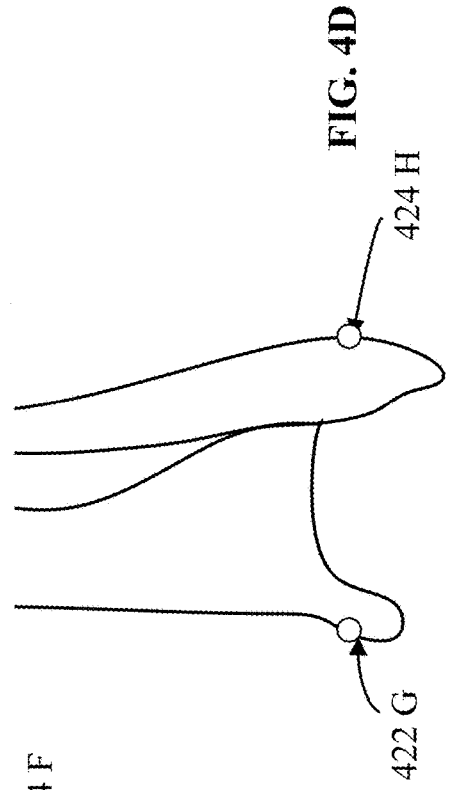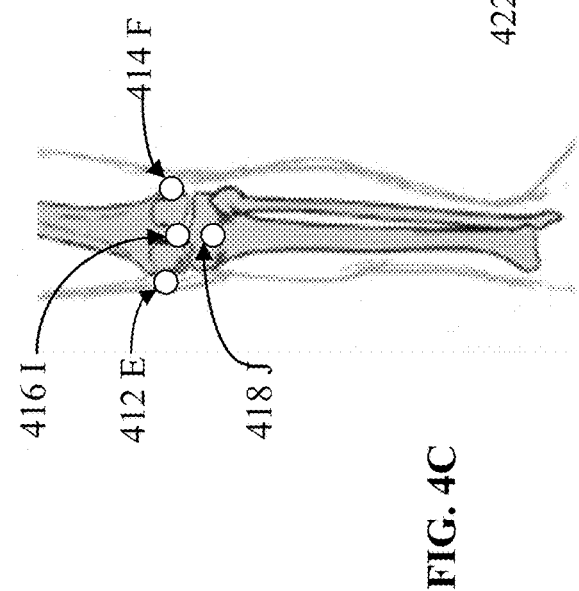
FIG. 4A  FIG. 4B  FIG. 4C  FIG. 4D

PINLESS NAVIGATION SYSTEM

BENEFIT CLAIM

This application claims the benefit of Provisional Application 63/245,256, filed Sep. 17, 2021, the entire contents of which is hereby incorporated by reference as if fully set forth herein, under 35 U.S.C. § 119(e). The applicants hereby rescind any disclaimer of claim scope in the parent application or the prosecution history thereof and advise the USPTO that the claims in this application may be broader than any claim in the parent application.

FIELD OF DISCLOSURE

One technical field of the present disclosure is a pinless navigation device provided to assist in medical surgeries such as arthroplasty, including a total hip replacement. Another technical field is a pinless angle finder and measuring device and using it in, for example, hip, knee, and shoulder replacement surgeries to guide surgical instruments to position, ream, saw, and drill during the surgeries. Another technical field is a pinless, skin based electronic digital angle finder and measuring device and using it to assist in surgeries including robotic assisted surgeries.

BACKGROUND

According to human hip anatomy, an acetabulum is a socket of a ball-and-socket hip joint. In a healthy hip, the ball fits securely inside the acetabulum socket and rotates easily within the smooth cartilage lining. However, a fracture of the acetabulum or the ball may cause painful injuries that may require surgeries.

During a surgery, such as hip arthroplasty (i.e., a total hip replacement procedure), before introducing an implant to the acetabulum socket, acetabular and femoral components of medical instruments are used to take measurements of the acetabulum socket either via manual instrumentation or with a computer-based navigation assistance. However, the manual instrumentation and visual estimation of the implant position in the socket are prone to human errors and inaccuracies. Furthermore, computer-based navigation often uses large, expensive, and complex systems that require that the surgeons are very well trained in using the systems.

According to another example, during knee arthroplasty (i.e., a knee replacement procedure), the cuts of the femur and tibia are usually made using mechanical manual jigs—which may be time consuming and error-prone. Furthermore, a computer-based navigation system used in the knee arthroplasty usually requires that the pins are drilled into a bone—which may be difficult and challenging to perform.

However, as in all arthroplasty procedures, an accurate implant positioning and accurate bone cutting are paramount in avoiding complications that could be related to, for example, the component's wear, hip dislocations, revision surgery, implant longevity, patient morbidity, and increased medical cost.

Therefore, there is a need for a navigation device that would not only be pinless, but that would also allow accurate measuring of the dimensions and position angles of human body anatomy for the purpose of performing surgeries.

SUMMARY

A computer-based, pinless navigation system disclosed herein comprises a primary unit that communicates with a plurality of wireless pinless skin based sensors. The sensors are placed at various locations on a patient's skin and in such a way that the sensors overlay bony prominences. The sensors are non-invasive as they are placed on the patient's skin without protruding or piercing the skin. The sensors may be wireless or wired and may be configured to communicate electronic signals carrying data to the pinless navigation system.

The primary unit of the pinless navigation system may include an electronic angle and distance finder device. The finder may receive electronic signals from the skin sensors and use the received signals to extract data that is included in the signals and that captures the relevant angles and distance measurements obtained by the sensors for the bony prominences. The measurements may be displayed on a computer-based display device and may be used by a surgeon to place accurately and precisely, for example, a hip implant in an acetabulum socket.

The system and the corresponding methods may be used to, for example, digitally determine a patient's anterior pelvic plane (described later in FIG. 2) based on the anterior superior iliac spine view (defined later) and identified while a patient is lying during a surgery in any position including lateral decubitus, lazy lateral, supine or prone positions. The system and the corresponding methods provide accurate and precise measurements of a patient's anterior pelvic plane, and horizontal axis of the pelvis as determined by the angle of inclination, and angle of forward flexion to a surgeon during the procedure of, for example, surgically implanting a hip prosthesis into a patient's hip socket.

In some implementations, a pinless navigation system is configured to help surgeons with precise and accurate placements of joint replacement implants. The pinless navigation system disclosed herein also allows the surgeons with precise and accurate cuts, reaming, and drilling of bones. Furthermore, the pinless navigation system allows to simplify the intraoperative navigation when performing, for example, a hip, knee, or shoulder arthroplasty, by use of wireless or wired sensors that provide information used to determine the corresponding angles and measurements for the surgical purposes.

Moreover, the pinless navigation system may be used to eliminate the need to visually estimate the correct placements of components during medical procedures. The skin based pinless position sensing technology of the pinless navigation system may be used to generate and provide input to, for example, a robotic-assisted surgery.

BRIEF DESCRIPTION OF THE DRAWINGS

FIG. 4A and FIG. 4B are frontal views of a pre-incision setup of a pinless navigation system for a hip replacement that employs sterilized wireless or wired sensors placed on a patient's skin overlying a bilateral anterior superior iliac spine and a pubic symphysis.

FIG. 4C and FIG. 4D are a frontal view of a pre-incision setup of a pinless navigation system for a knee replacement that employs sterilized wireless or wired sensors placed on a patient's skin.

DESCRIPTION OF EXAMPLE EMBODIMENTS

Figure 1A:
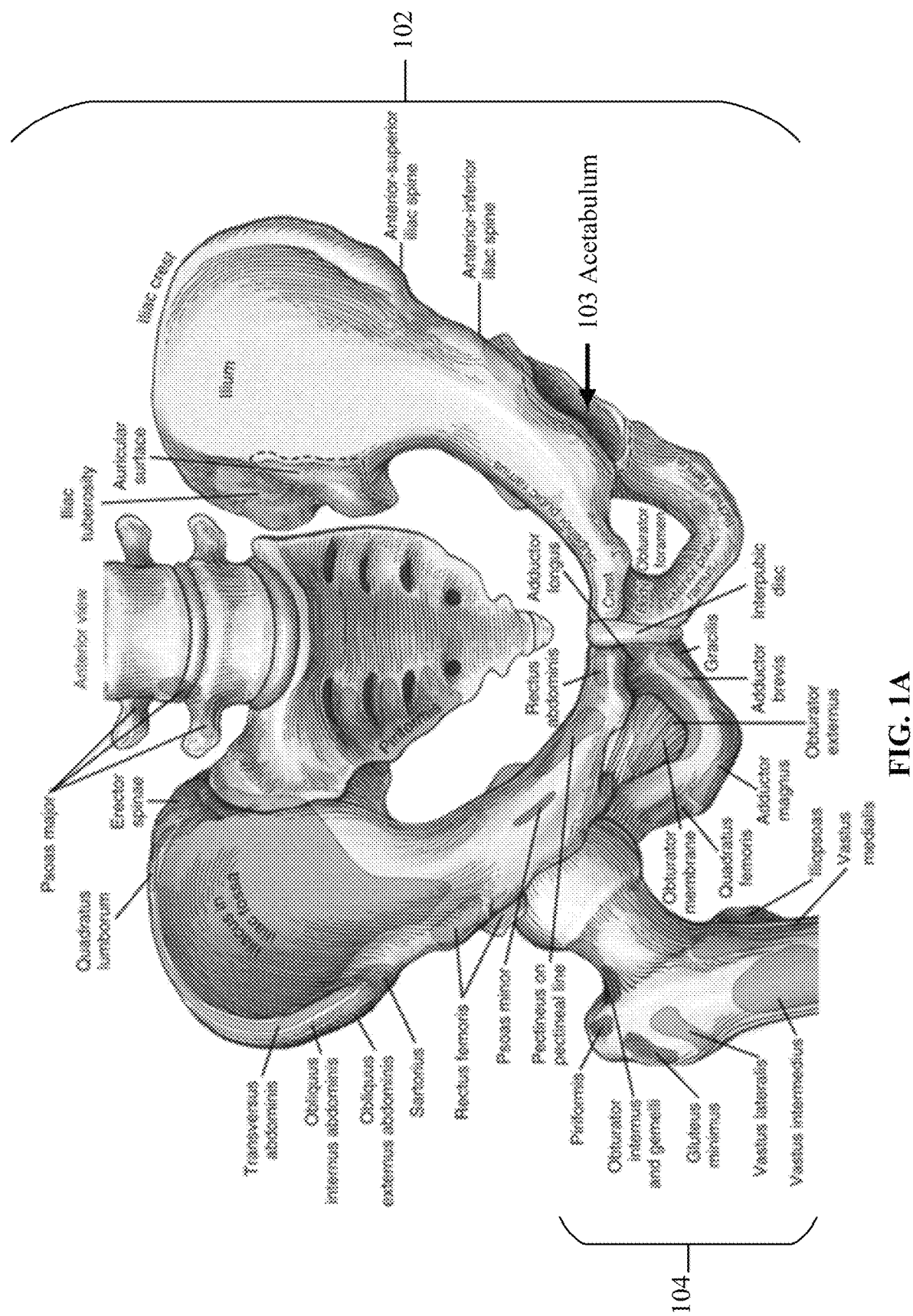
FIG. 1A is an anteroposterior view of a native pelvis and an associated proximal femur including a femoroacetabular articulation.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein according to the following outline:

1.0. INTRODUCTION TO A PINLESS NAVIGATION SYSTEM
2.0. TERMINOLOGY RELATED TO ANATOMY OF A HUMAN PELVIS
3.0. ACCURACY OF ACETABULUM MEASUREMENTS
4.0. ACETABULAR COMPONENT
5.0. PRE-INCISION SETUP
  5.1. HIP ARTHROPLASTY CASE
  5.2. KNEE ARTHROPLASTY CASE
  5.3. SHOULDER ARTHROPLASTY CASE
6.0. PINLESS NAVIGATION SYSTEM
  6.1. PRIMARY UNIT
  6.2. SKIN SENSORS
  6.3. INTRA-INCISIONAL GREATER TROCHANTER SENSOR
7.0. EXAMPLE FLOW CHART OF AN EXAMPLE PROCESS
8.0. IMPLEMENTATION MECHANISMS 1.0. Introduction to a Pinless Navigation System A pinless navigation system described herein comprises a primary unit equipped with a display screen and communicating with pinless skin based sensors. The screen may be used to display real time angle measurements determined for, for example, an implant placement during an arthroplasty procedure. The measurements may be determined based on position information determined and provided by the pinless skin based sensors placed on a patient's skin. The sensors may be wireless or wired and may be non-intrusively positioned on the skin on bony prominences.

The pinless navigation system may be configured to execute steps of the methods for assisting surgeons in performing arthroplasty procedures. The methods allow a surgeon to, for example, position implants accurately, precisely, and intraoperatively in bony cuts. Examples of the implants include a hip replacement implant, a knee replacement implant, a shoulder replacement implant, and the like. The methods also allow to ream a patient's bone with the standalone navigation or robotic assisted joint replacement based on the information collected and provided by the pinless skin based position input sensors.

The methods described herein may be used to assist a surgeon in an intraoperative positioning of a replacement implant during an arthroplasty procedure, and/or assisting in bony cuts or reaming of bone in a patient using, for example, a standalone navigation system or a robotic assisted joint replacement system via novel pinless wireless or wired skin based input sensors.

2.0. Terminology Related to Anatomy of a Human Pelvis

Terminology included below is provided to assist in understanding the intricacies and functionalities of a novel pinless navigation system unit presented later. Indeed, by way of introduction, included below are a brief description of anatomy of a human pelvis and a brief description of arthroplasty medical procedures, to which the pinless navigation system pertains. Also provided herein is a brief description of traditional ways of placing an acetabular component in an acetabulum socket for taking measurements of the pelvis for the purpose of performing the arthroplasty surgeries.

The drawing figures, and all of the description and claims in this disclosure are intended to present, disclose, and claim a technical system and technical methods in which specially programmed computers, using a special-purpose distributed computer system design, execute functions that have not been available before to provide a practical application of computing technology to the problem of machine learning model development, validation, and deployment. In this manner, the disclosure presents a technical solution to a technical problem, and any interpretation of the disclosure or claims to cover any judicial exception to patent eligibility, such as an abstract idea, mental process, method of organizing human activity or mathematical algorithm, has no support in this disclosure and is erroneous.

Figure 1B:
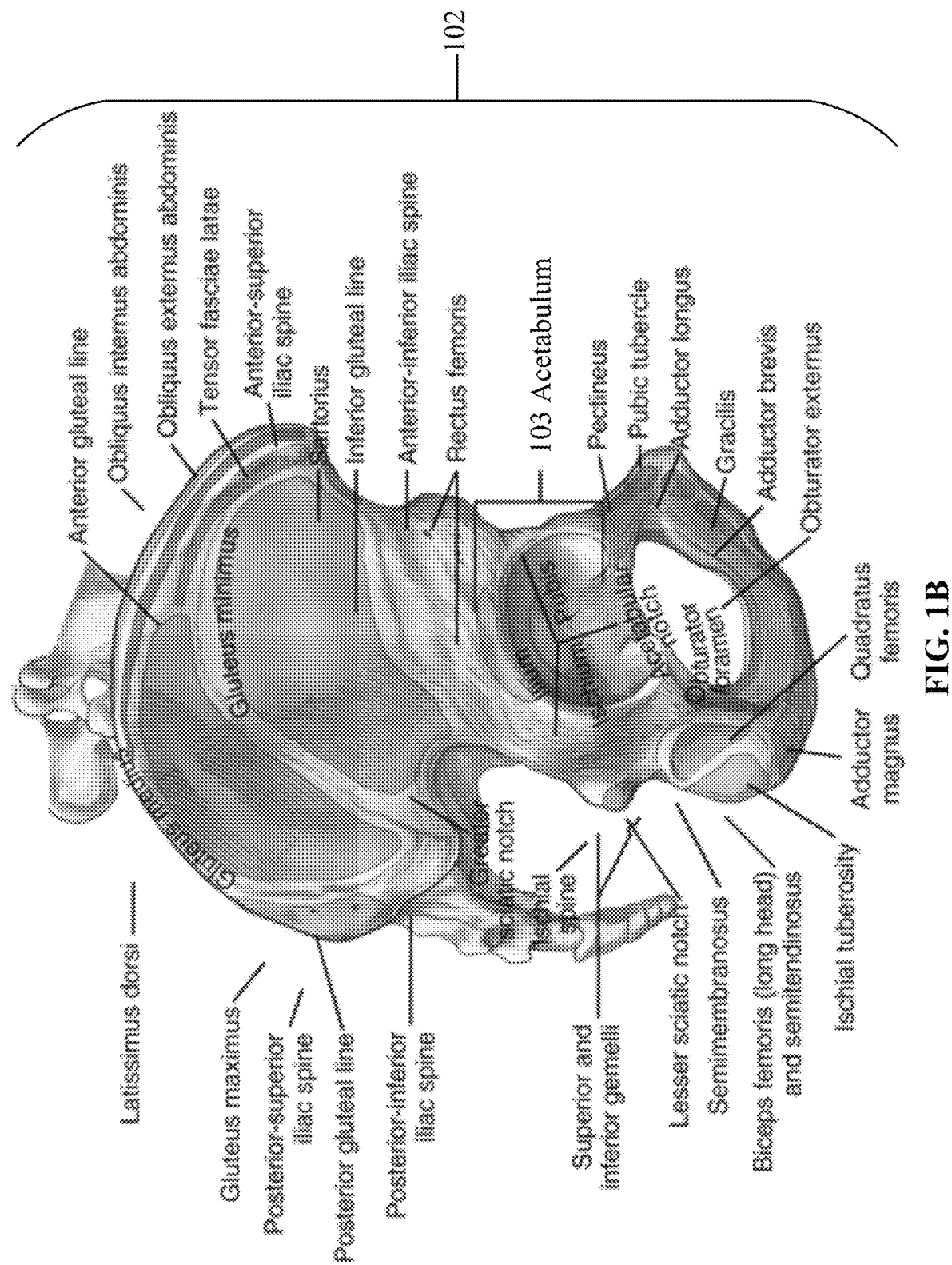
FIG. 1B is a side view of a position of the acetabulum relative to a pelvis and an anterior pelvic plane that is used to guide acetabular implant positioning.

The simplified anatomy of a human native pelvis is described in FIG. 1A and FIG. 1B. FIG. 1A is from Neumann D A: Kinesiology of the musculoskeletal system: foundations for physical rehabilitation, ed 2, St Louis, 2010, Mosby, FIG. 12-1. FIG. 1B is from Neumann D A: Kinesiology of the musculoskeletal system: foundations for physical rehabilitation, ed 2, St Louis, 2010, Mosby, FIG. 12-2.

FIG. 1A is an anteroposterior (AP) view of a native pelvis and an associated proximal femur including a femoroacetabular articulation. More specifically, FIG. 1A illustrates a human pelvis 102, an associated proximal femur 104 (including a femoroacetabular articulation), and an acetabulum 103 in pelvis 102. However, for the clarity of the description, other elements of the pelvis (depicted in FIG. 1A-1B) are not labeled with numerals because those elements are not further referred to and are not critical for describing and understanding the pinless navigation system presented herein.

From the anatomical point of view, a human hip joint includes a ball and a socket joint. The socket part is lined with smooth cartilage included in acetabulum 103, which is part of the pelvis. A fracture of the socket is usually referred to as an acetabular fracture. Such fractures are far less common than fractures to the ball part of the joint.

Referring now to FIG. 1B, the figure is a side view of a position of acetabulum 103 relative to native pelvis 102 and an anterior pelvic plane that is used to guide positioning of the acetabular implant.

Figure 2:
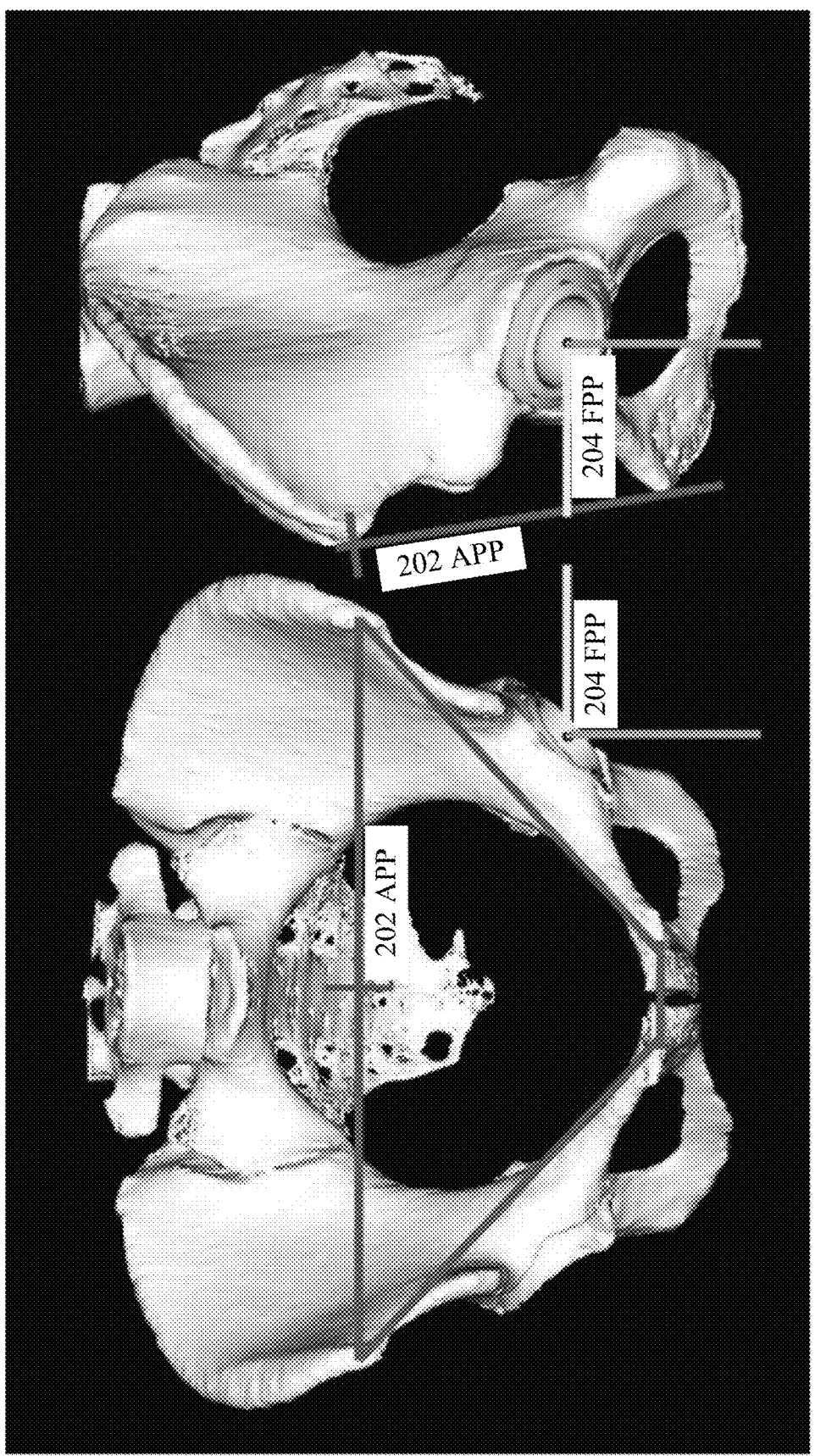
FIG. 2 illustrates an example position of an acetabulum relative to a pelvis and an anterior pelvic plane (APP) which is used to guide acetabular implant positioning.

FIG. 2 illustrates an example position of an acetabulum relative to a pelvis and an anterior pelvic plane (APP) which is used to guide acetabular implant positioning. The two snapshots depicted in FIG. 2 are two different views of the same technique.

In FIG. 2, an APP 202 corresponds to an anterior pelvic plane. APP 202 is the reference plane for placement of the acetabular component, and its description and special relationship are detailed in the orthopedic literature.

APP 202 is a plane in which the sensors of the pinless navigation system are placed along the bony pelvis to recreate the APP. FIG. 2 demonstrates a position of the acetabulum relative to a pelvis and APP 202 that is used to guide acetabular implant positioning.

An FPP 204 is a functional pelvic plane, which is another frame of reference for the human pelvis.

For brevity of the description, the terminology related to anatomy of a human knee and the terminology related to anatomy of a human shoulder are omitted herein but are detailed in the medical books and publications.

3.0. Accuracy of Acetabulum Measurements

Total hip arthroplasty has become one of many successful interventions in the history of medicine. After the arthroplasty, over time, a patient may regain some range of motion and function, and some relief from pain.

Accurate biomechanical reconstruction of a hip joint is essential to achieve an overall function and longevity, with the acetabular positioning being a key factor. However, the accurate arthroplasty depends, to some extent, on obtaining accurate measurements of, for example, a patient's acetabulum socket and the socket position in relation to other parts of the patient's pelvis.

Part of a hip arthroplasty procedure is positioning an acetabular implant in a patient's acetabulum socket. The pelvic tilt plays a major role in the functional positioning of the acetabulum. Furthermore, positioning an acetabular cup in the patient's acetabulum socket has a significant impact on the results of the hip arthroplasty as it may affect the dislocation, abductor muscle strength, gait, limb lengths, impingement, noise generation, range of motion, wear, loosening, cup failure, and the like.

However, commonly used techniques for positioning the implant in the acetabulum socket often fail to provide enough information about the real orientation of the patient's pelvis as the patient is, for example, prepared for a surgery and resting on an operating table.

The variables in the cup position include a depth, height, and angular position (including the anteversion and inclination, both described later). The implications of a change in the depth of the center of rotation include, among others, a medialized positioning versus an anatomical positioning. The traditional medialization provides several beneficial effects on joint reaction force. However, the anatomical positioning is increasingly recognized as providing additional beneficial effects.

The pinless navigation system presented herein provides the functionalities for obtaining more accurate measurements than those provided using, for example, traditional surgical techniques.

4.0. Acetabular Component

In some implementations, a pinless navigation system described cooperates with an acetabular component. The acetabular component may be used to, for example, take measurements, or approximate the measurements, of an appropriate position of the acetabular component with respect to an acetabulum socket prior to performing a hip-replacement arthroplasty. An example way in which the acetabular component may be placed in the acetabulum socket using a standard inserter via a manual technique and a manual guide was described in FIG. 2 and is further described in FIG. 3A-3B.

Figure 3A:
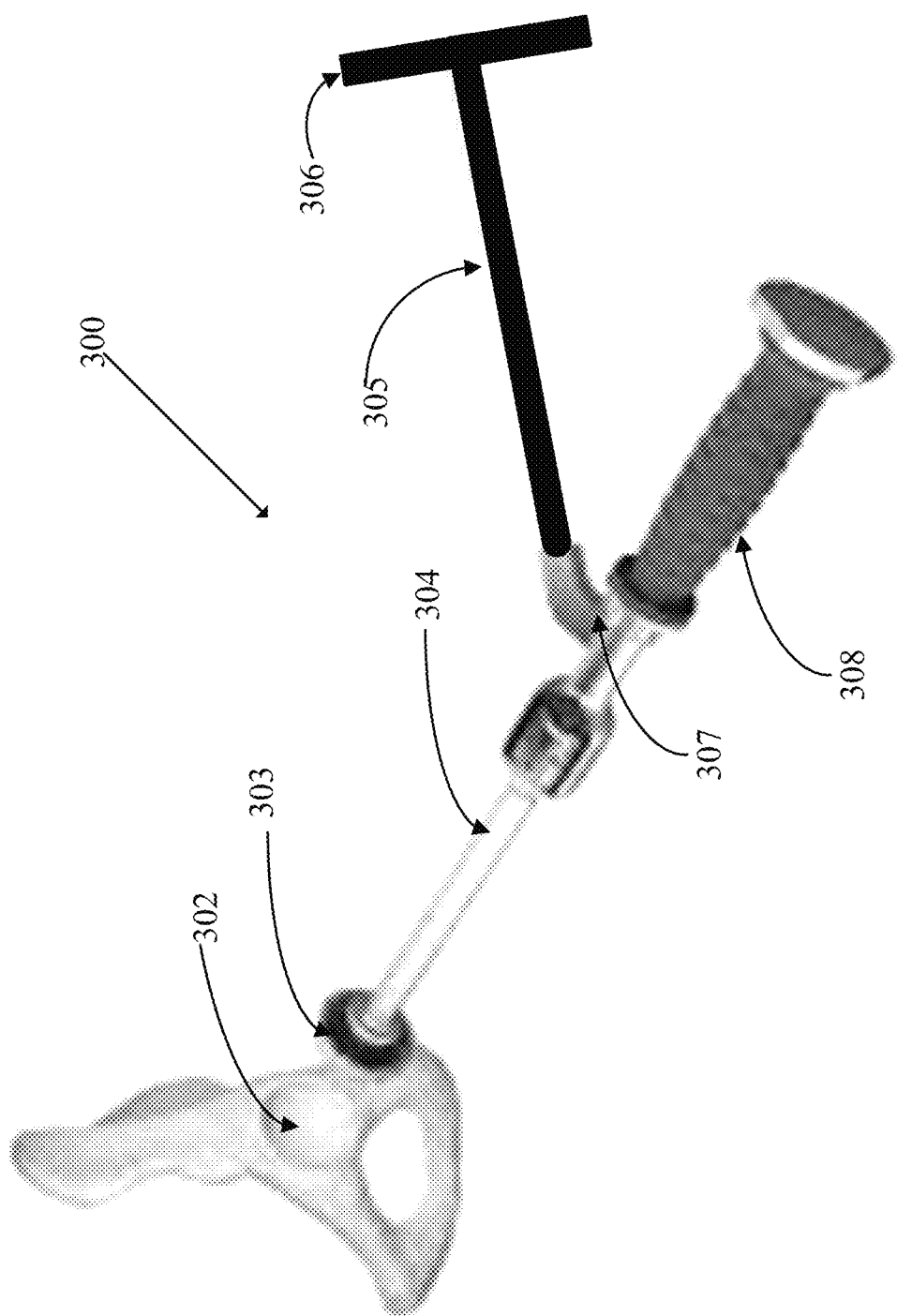
FIG. 3A and FIG. 3B illustrate an example of a way in which an acetabular component is placed using a standard inserter via a manual technique and a manual guide to approximate an appropriate acetabular component position.
Figure 3B:
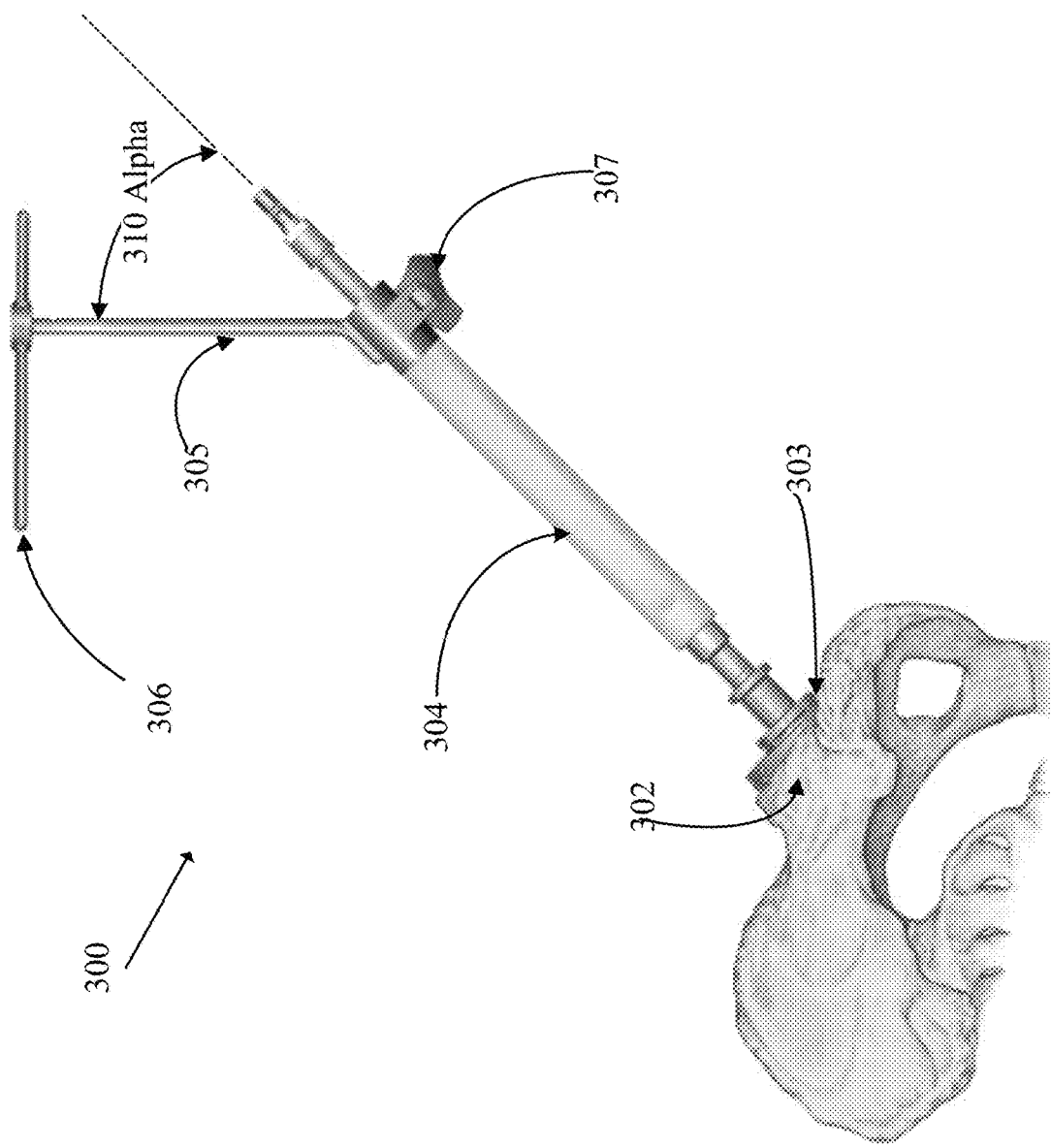

FIG. 3A and FIG. 3B illustrate an example of a way in which an acetabular component 303 is placed using a standard inserter 300 via a manual technique and a manual guide to approximate an appropriate acetabular component position. In FIG. 3A-3B, an acetabular component 303 is placed in an acetabulum opening 302 of a human pelvis. Acetabular component 303 may be connected to an arm 304 (also called a rod), which may be attached, via an adapter clip 307 and via an arm extension 305, to a primary unit 306 (described later).

Arm 304 may also include a handle 308, which allows a surgeon to hold, or grip on, the inserter.

FIG. 3B further depicts an angle alpha 310 between the direction of arm 304 and arm extension 305. Angle alpha 310 depends on the implementations. In some implementations, angle alpha 310 is 45 degrees. However, that specific angle is neither mandatory nor essential, and it does vary.

5.0. Pre-Incision Setup

5.1. Hip Arthroplasty Case

FIG. 4A, 4B, 4C, 4D are planar views of a pre-incision setup of a pinless navigation system for a hip replacement that employs sterilized wireless or wired sensors placed on a patient's skin overlying a bilateral anterior superior iliac spine and a pubic symphysis.

An anterior superior iliac spine (ASIS) is a bony projection of the iliac bone. It refers to the anterior extremity of the iliac crest of the pelvis. It provides an attachment for the inguinal ligament and the sartorius muscle.

A pubic symphysis (C) is a joint sandwiched between a left pelvic bone and a right pelvic bone of a human pelvis. It helps the pelvis to absorb some of a patient's weight from the upper body before the weight is distributed to the lower body.

Referring again to FIG. 4A-4B, 4C, 4D the figures depict different frontal views of the same pre-incision setup of the pinless navigation system for a hip replacement that employs sterilized wireless or wired sensors 402A and 404B placed on the skin overlying the bilateral anterior superior iliac spines (ASIS) and a sensor 406C placed over the pubic symphysis (C). Optionally, an additional sensor 408D may be placed over the sacrum.

5.2. Knee Arthroplasty Case

FIGS. 4C and 4D is a frontal view of a pre-incision setup of a pinless navigation system for a knee replacement that employs sterilized wireless or wired sensors placed on a patient's skin. The sensors may be placed on the skin around the knee and may include a sensor 412E overlying the bilateral medial epicondyle, and a sensor 414F overlying the lateral femoral epicondyle. Optionally, an additional sensor 416I may be placed over the mid portion of the patellae and an additional sensor 418J may be placed over the tibial tubercles.

5.3. Shoulder Arthroplasty Case

Pre-incision setup of a pinless navigation system for a shoulder replacement that employs sterilized wireless or wired sensors placed on a patient's skin. The sensors may be placed on the skin around the shoulder and may include sensors overlying the coracoid, scapula, acromion, elbow.

6.0. Pinless Navigation System

In some implementations, a pinless navigation system presented herein comprises a primary unit and pinless skin sensors. The skin sensors may be, for example, standalone sensors that may be manually placed on a patient's skin.

Figure 5A:
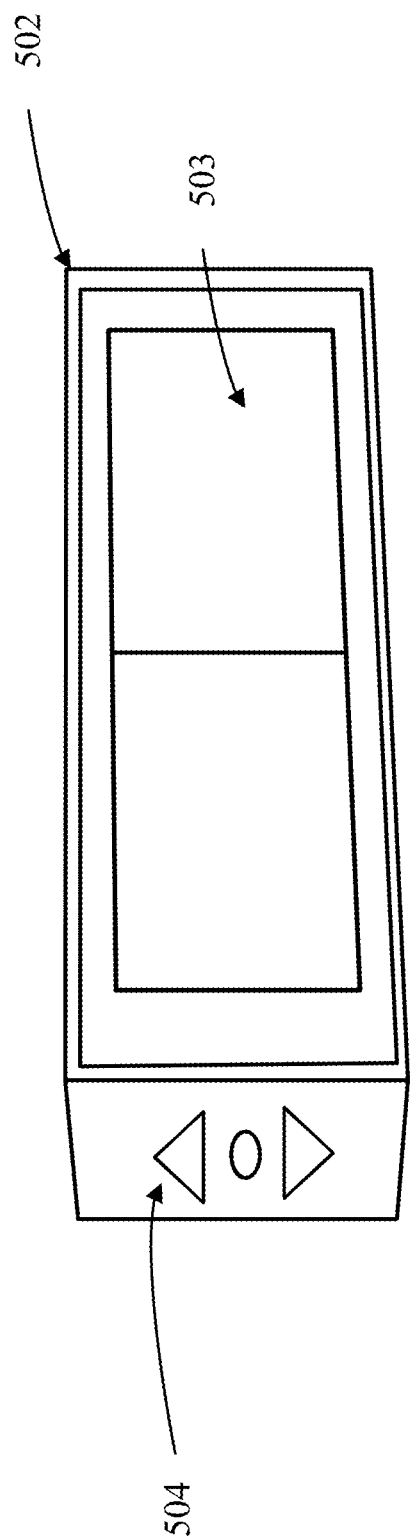
FIG. 5A is a perspective view of a primary unit that is used by a pinless navigation system, according to some implementations.

An example primary unit is described in FIG. 5A.

6.1. Primary Unit

FIG. 5A is a perspective view of a primary unit 502 that is used by a pinless navigation system, according to some implementations. Primary unit 502 may include a display 503, one or more controls 504 or knobs, and computer-based components (not shown) that are located inside unit 502 and configured to execute program instructions for performing the functions implemented in primary unit 502.

In some implementations, a primary unit may be constructed from, for example, any sterilizable material such as metal, plastic, or composite material commonly used in operating rooms.

The primary unit may connect to sensors (described later) either wirelessly or via a wire. If the primary unit is configured with the wireless connectivity, then the primary unit may wirelessly connect via Bluetooth or radio waves or some other wireless means with various sensors such as sensors placed on a patient's skin over bony landmarks and intra-incisional sensors placed over, for example, a greater trochanter. The primary unit may also connect via wires to other sensors, a battery source, and other units.

The primary unit may use the data relayed by the sensors in many different ways. For example, the primary unit may use the data to calculate an acetabular component anteversion and inclination for the purpose of performing an arthroplasty procedure. The primary unit may also use the data to calculate femoral stem anteversion, varus/valgus position of the femoral stem, and bilateral leg lengths.

Anteversion means leaning forward. Stating differently, anteversion is defined as the angle between the transverse axis and the acetabular axis when projected onto the transverse plane. Femoral anteversion is a condition in which the femoral neck leans forward with respect to the rest of the femur. This causes the leg to rotate internally, so that the knee and foot twist toward the midline of the body.

Anatomical inclination is defined as the angle between the acetabular axis and the longitudinal axis. The terms valgus and varus refer to angulation (or bowing) within the shaft of a bone or at a joint in the coronal plane. The terms varus and valgus always refer to the direction to which the distal segment of the joint points.

Figure 6:
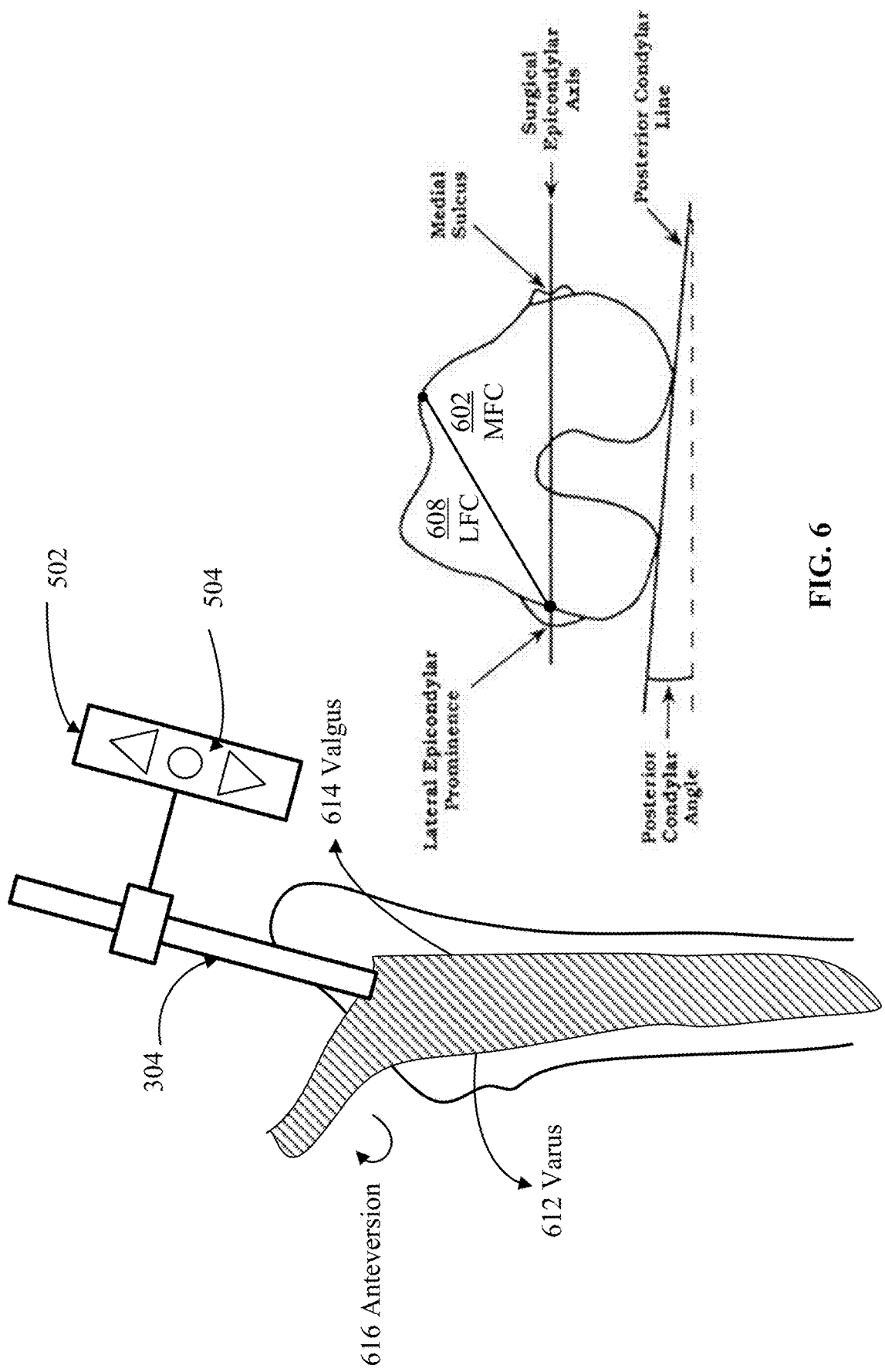
FIG. 6 is a schematic view of a pinless navigation system used to calculate femoral stem anteversion, varus/valgus position of the femoral stem, and bilateral leg lengths, according to some implementations.

FIG. 6 is a schematic view of a pinless navigation system used to calculate a femoral stem anteversion 616, a varus 612 position, a valgus 614 position of the femoral stem, and bilateral leg lengths, according to some implementations. The terms used in some implementations are a lateral epicondyle (LE), a medial epicondyle (ME), a lateral femoral condyle LFC 608, and a medial femoral condyle MFC 602.

The right lower corner of FIG. 6 shows a diagram of the axial view of the right distal femur as seen from below by the surgeon during a total knee arthroplasty with the knee flexed at 90°. This diagram is from: Berger R A, Rubash H, Seel M, Thompson W, Crossett L. Determining the rotational alignment of the femoral component in total knee arthroplasty using the epicondylar axis. Clin Orthop. 1983; January (286): 40-7. Lippincott Williams & Wilkins.

The primary unit may use the data received from the sensors to calculate a femoral component anteversion and coronal alignment in the case of a hip replacement. The primary unit may also use that data to calculate changes in a leg length and a hip offset, both of which provide important information for performing, for example, a hip replacement procedure.

The primary unit may also use the data received from the sensors to calculate limb mechanical and anatomic axis, angles of tibial and femoral cuts and femoral and a tibial component positioning in terms of flexion, extension, rotation, and slope of components, all of which are useful in, for example, a knee replacement surgery. In addition, the primary unit may use that data to calculate glenoid version, flexion, extension, rotation as well as humeral component angulations in terms of flexion, extension, rotation, and slope of components in terms of shoulder replacement. The primary unit may act as a position sensor for determining, for example, a femoral/acetabular implant position.

In some implementations, the primary unit includes a battery source or wired connection to the battery source. It may also include unique hardware/software to process, for example, alterations in angulation in all 3 axes and to process alterations in the distance between the assorted sensors.

The primary unit may be equipped with a user interface and/or a user-friendly display monitor that displays the different angular and distance measurements that have been registered. The user interface may be, for example, configured to display the desired angulation of the implants/components and whether the desired angulation has been achieved.

In some implementations, the primary unit has a clip/snap/screw-on component that facilitates attaching the primary unit to any component/implant, inserter, holder, reamer, drill, saw, or screwdriver. Specifically, the primary unit may be attached to a universal adapter clip (element 307 in FIG. 3A-3B) that can be attached to an arm (or a rod) of any inserter device.

Typically, the primary unit implements several functionalities, including providing the operator with real time component position data, and acting as a position sensor for a component positioning determined by, for example, an embedded accelerometer and/or gyroscope unit. The primary unit may also act as the central processing unit for the entire device.

In some embodiments, the primary unit further includes a position sensor implemented in the primary unit itself. The position sensor may be used to determine a humeral/glenoid component position.

6.2. Skin Sensors

A primary unit of a pinless navigation system may communicate with a plurality of sensors. Some of the sensors are pinless skin based sensors and are called that way because they can be simply placed on a patient's skin without the use of any pins. Placing the pinless sensors on the skin does not involve puncturing and otherwise protruding or puncturing the patient's skin.

The technology implemented in the pinless skin based sensors is novel because it allows, among other things, to obtain angular and distance related measurements of bony prominences in a human body without using any pins or other skin-penetrating objects. The measurements obtained by the pinless sensors may be transmitted to the primary unit to cause the unit to calculate, for example, a hip/knee/shoulder replacement component position relative to the corresponding mechanical and anatomical axes. In some implementations, at least three sensors work in tandem to obtain the measurements.

Examples of pinless sensors 402A-422G were described in FIG. 4A-4D. The sensors 402A-422G may be placed on a patient's skin at various locations to probe the locations and to collect measurements data. The sensors may generate electronic signals comprising the data and may transmit the signals to a primary unit. Upon receiving the signals with the data, the primary unit may extract the data from the signals and use the data to, for example, determine an acetabular component inclination and anteversion relative to the anterior pelvic plane.

The sensors may communicate with the primary unit either wirelessly or via wires. The wireless or wired skin based sensors could be attached to the skin overlying the bony prominences including the right anterior superior iliac spine, left anterior superior iliac spine right patella, left patella, right tibial tubercle, left tibial tubercle, right tibial crest, left tibial crest, right knee medial epicondyle, right knee lateral epicondyle, left knee medial epicondyle, left knee lateral epicondyle, right medial malleolus, right lateral malleolus, left medial malleolus, left lateral malleolus, right heel, left heel, and the like.

Figure 5B:
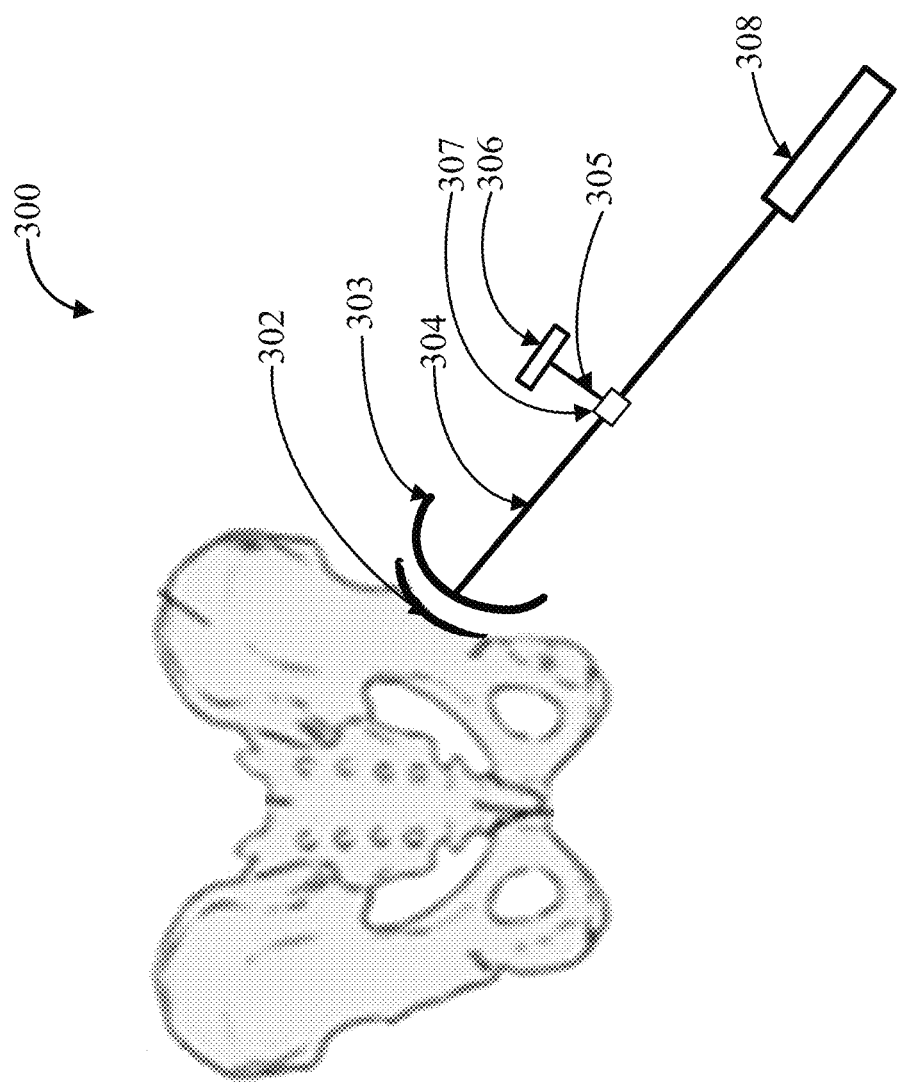
FIG. 5B illustrates an example possible assembly for a primary unit that is mounted on a standard cup inserter handle.

FIG. 5B illustrates an example possible assembly for a primary unit that is mounted on a standard cup inserter handle. FIG. 5B shows the navigation device assembled to the acetabular cup being inserted into the pelvis should remain.

As also shown in FIG. 3A, acetabular component 303 in FIG. 5B is placed in an acetabulum opening 302 of a human pelvis. Acetabular component 303 may be connected to arm 304, which may be attached, via adapter clip 307 and arm extension 305, to primary unit 306. Arm 304 may also include handle 308, which allows a surgeon to hold, or grip on, the inserter.

A pinless skin based sensor may work in tandem with other sensors to sense its own individual sensor's position relative to positions of other sensors and to a patient's mechanical and anatomical axes in real time. This allows for a real time assessment of the mechanical and anatomical axes should a patient's leg move during surgery thereby altering the maneuvers needed for the safe placement of, for example, the knee replacement components or bony cuts.

The wireless or wired skin based sensors could be attached to the skin overlying the bony prominences including, for example, right anterior superior iliac spine, left anterior superior iliac spine, and midline of the pubis. Attaching the sensors in those places allows the sensors to collect the data to be used to calculate each patient's unique anterior pelvic plane.

Some of the sensors may act as principal sensors that may be placed to calculate the patient's anterior pelvic plane, and accessory optional sensors that can collect additional information.

In some implementations, the sensors include three principal sensors that are used to assure the proper use of the device. These sensors may be placed on the midline of the sacrum, right greater trochanter, left greater trochanter, right patella, left patella, right tibial tubercle, left tibial tubercle, right knee medial epicondyle, right knee lateral epicondyle, left knee medial epicondyle, left knee lateral epicondyle, right medial malleolus, right lateral malleolus, left medial malleolus, left lateral malleolus, right heel, left heel, and the like.

Optionally, the sensors may also acquire the acetabular version, abduction, femoral offset, femoral transepicondylar axis, combined anteversion and limb length, and the like.

A wireless or wired skin sensor may include an accelerometer and a gyroscope, both included in the housing of the sensor. The skin sensor may also include a battery and a communications interface, such as Bluetooth, radiofrequency, or other forms of wireless or wired information transmission.

The sensors may communicate with a primary unit of the pinless navigation system continuously to provide real time location information of all bony prominences that are of interest or that have been marked.

The sensors may be constructed from, for example, sterilizable metal, plastic, or composite material commonly used in operating rooms. The sensors may be sterilized themselves, or they may be housed in a sterile adhesive dressing that prevents contamination of the surgical field but allows for the intraoperative placement.

Figure 8:
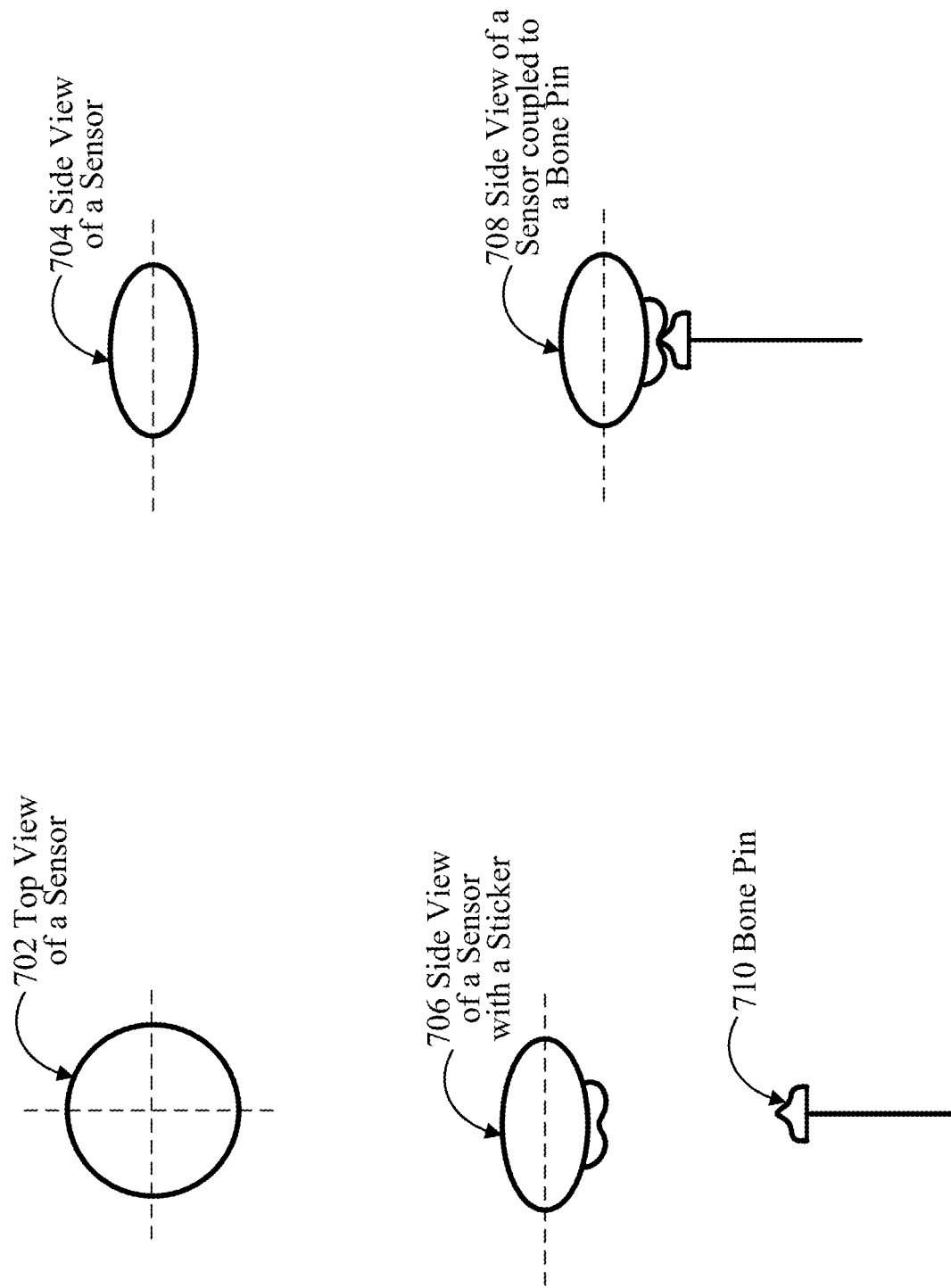
FIG. 8 shows several schematic views of wireless or wired sensor units and their corresponding stickers that are used to attach the sensor units to a skin.

FIG. 8 shows several schematic views of wireless or wired sensor units and their corresponding stickers that are used to attach the sensor units to a skin or to bone pin. The example views include a top view 702 and a side view 704. Additional views include a side view 706 of a sensor comprising a sticker, and a side view 708 of a sensor coupled to a bone pin 710.

In some implementations, a sensor is shaped as a disk (or an ellipsoid). But, generally, the shapes of the sensors may range from a circular, to a rectangular, to a cube, or to triangular. Typically, the sensors are small, and their sizes may range from 0.1 inches in diameter up to 4 inches in diameter. The sensor's height may range from 0.1 inches up to 4 inches.

The sensor may have attached a sticker, which may have a shape of a hashed square. The sticker may allow attaching the sensor to, for example, a patient's skin, a bone pin, and the like.

The sensors may communicate wirelessly or via wires with each other along the bilateral anterior superior iliac spines (ASIS) and the pubic symphysis for hip replacement. Additional sensors may be placed over the posterior sacrum, bilateral medial and lateral femoral epicondyles, medial and lateral malleoli, and potentially the mid portion of the patellae or the tibial tubercles exist with this system. Placement along the medial and lateral malleoli, tibial crest, tibial tubercle, and the center of the tibia are important for a knee replacement. Placement of sensors along the scapular spine, and coracoid and acromion, and/or greater tuberosity and/or glenoid and/or clavicle are important for a shoulder replacement.

The sensors may communicate wirelessly or via wires with the primary unit to calculate acetabular component anteversion and inclination, femoral component anteversion and coronal alignment, and changes in the leg length and hip offset.

The sensors may require a battery source and unique hardware/software to process alterations in angulation in all 3 axes and to also process alterations in distance between the assorted sensors.

6.3. Intra-Incisional Greater Trochanter Sensor

In some implementations, a pinless navigation system comprises a sensor called an intra-incisional greater trochanter sensor. That sensor can be placed on a greater trochanter prior to a femoral neck cut for a total hip replacement to determine, for example, an offset of the native hip joint.

Figure 7:
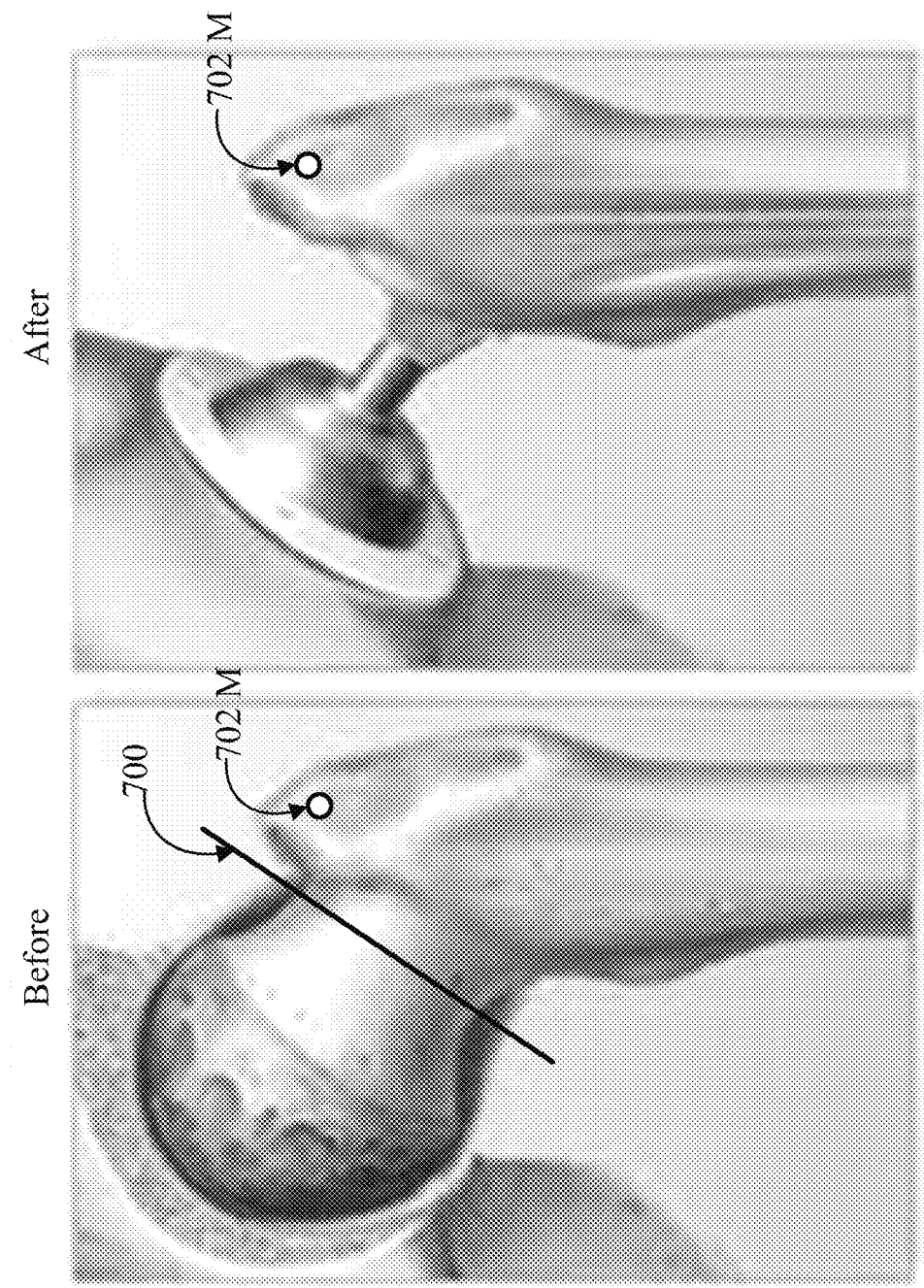
FIG. 7 is a schematic view of using an additional intra-incisional sensor placed on a greater trochanter prior to a femoral neck cut for a total hip replacement to determine an offset of a native hip joint, according to some implementations.

FIG. 7 is a schematic view of using an additional intra-incisional sensor placed on a greater trochanter prior to a femoral neck cut 700 for a total hip replacement to determine an offset of a native hip joint, according to some implementations. The intra-incisional greater trochanter sensor may remain in place 702M while trial/final components are utilized to help a surgeon to quantify changes in the offset relative to a preoperative native femoral offset. The intra-incisional greater trochanter sensor may be also used to provide data for, for example, a leg length calculations.

The intra-incisional greater trochanter sensor may be made as a replica of, for example, the skin sensors but may have a button/clip/fastener that allows it to be fixed to a small diameter metal tack/pin/screw that can be placed onto the greater trochanter.

7.0. Example Flow Chart of an Example Process

Figure 9:
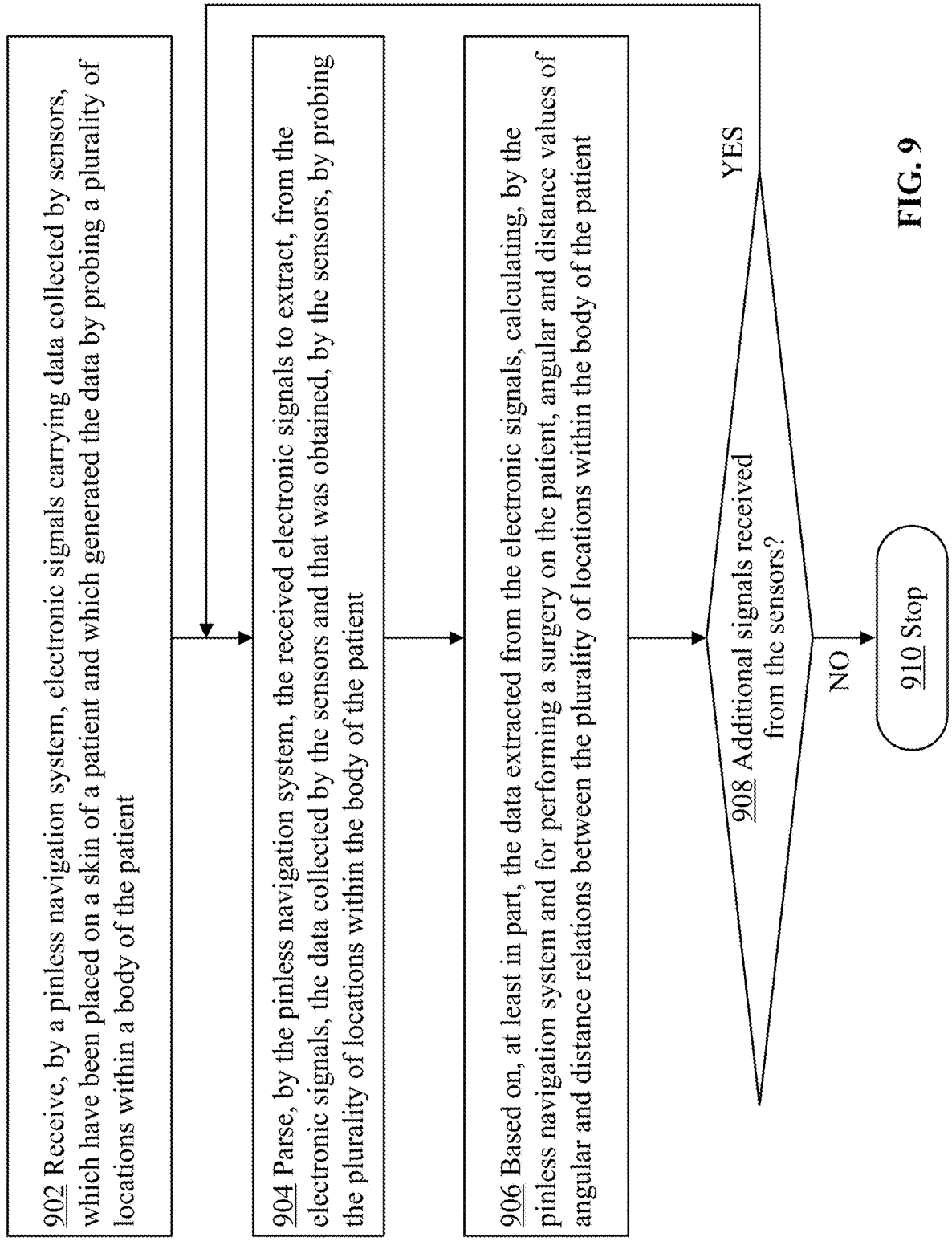
FIG. 9 is a flow chart depicting an example process for using a pinless navigation system.

FIG. 9 is a flow chart depicting an example process for using a pinless navigation system. The steps described in FIG. 9 may be performed by, for example, a primary unit of the pinless navigation system, or any other unit cooperating with, or included in, the pinless navigation system. For brevity of the description, it is assumed herein that the steps described in FIG. 9 are performed by the primary unit.

In step 902, a primary unit receives electronic signals carrying data collected by sensors. The sensors are pinless and are placed on a patient's skin. The sensors generate the data by probing a plurality of locations within the patient's body. The sensors are usually placed on bony prominences on the patient's body, and in such a way that placing the sensors on the skin does not include protruding or puncturing of the patient's skin.

In some implementations, the sensors comprise an accelerometer and gyroscope. Each sensor may be configured to transmit the data, collected by the accelerometer and the gyroscope of the sensor, to the pinless navigation system. The data may be transmitted via a wire or wirelessly via Bluetooth or any other wireless protocol that the primary unit implements.

The data received by the primary unit may also include trochanter data received from an intra-incisional greater trochanter sensor. The trochanter data may be collected prior to a femoral neck cut for a total hip arthroplasty to determine an offset of a native hip joint.

In step 904, the primary unit parses the received electronic signals to extract, from the electronic signals, the data collected by the sensors and that was obtained, by the sensors, by probing the plurality of locations within the patient's body.

In step 906, the primary unit calculates, based on, at least in part, the data included in the electronic signals, angular and distance values of angular and distances determined based on relations between the plurality of locations within the patient's body.

In some implementations, the plurality of locations includes any one of: posterior sacrum, bilateral medial and lateral femoral epicondyles, medial and lateral malleoli, a mid-portion of a patellae or a tibial tubercle. The angular and distance values may include any one of: femoral component anteversion and a coronal alignment, changes in a leg length, changes in a hip offset, or other. The angular and distance values may be displayed on a display device communicatively coupled to the pinless navigation system.

In step 908, the primary unit tests whether any additional electronic signals have been received from the sensors. If the additional electronic signals have been received, then the primary unit proceeds to perform step 904, described above. However, if no additional electronic signals have been received, then the primary unit, in step 910, stops executing its steps.

8.0. Implementations Mechanisms

Although the flow diagrams of the present application depict a particular set of steps in a particular order, other implementations may use fewer or more steps, in the same or different order, than those depicted in the figures.

According to one embodiment, the techniques described herein are implemented by one or more special-purpose computing devices. The special-purpose computing devices may be hard-wired to perform the techniques or may include digital electronic devices such as one or more application-specific integrated circuits (ASICs) or field programmable gate arrays (FPGAs) that are persistently programmed to perform the techniques or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices or any other device that incorporates hard-wired and/or program logic to implement the techniques.

Figure 10:
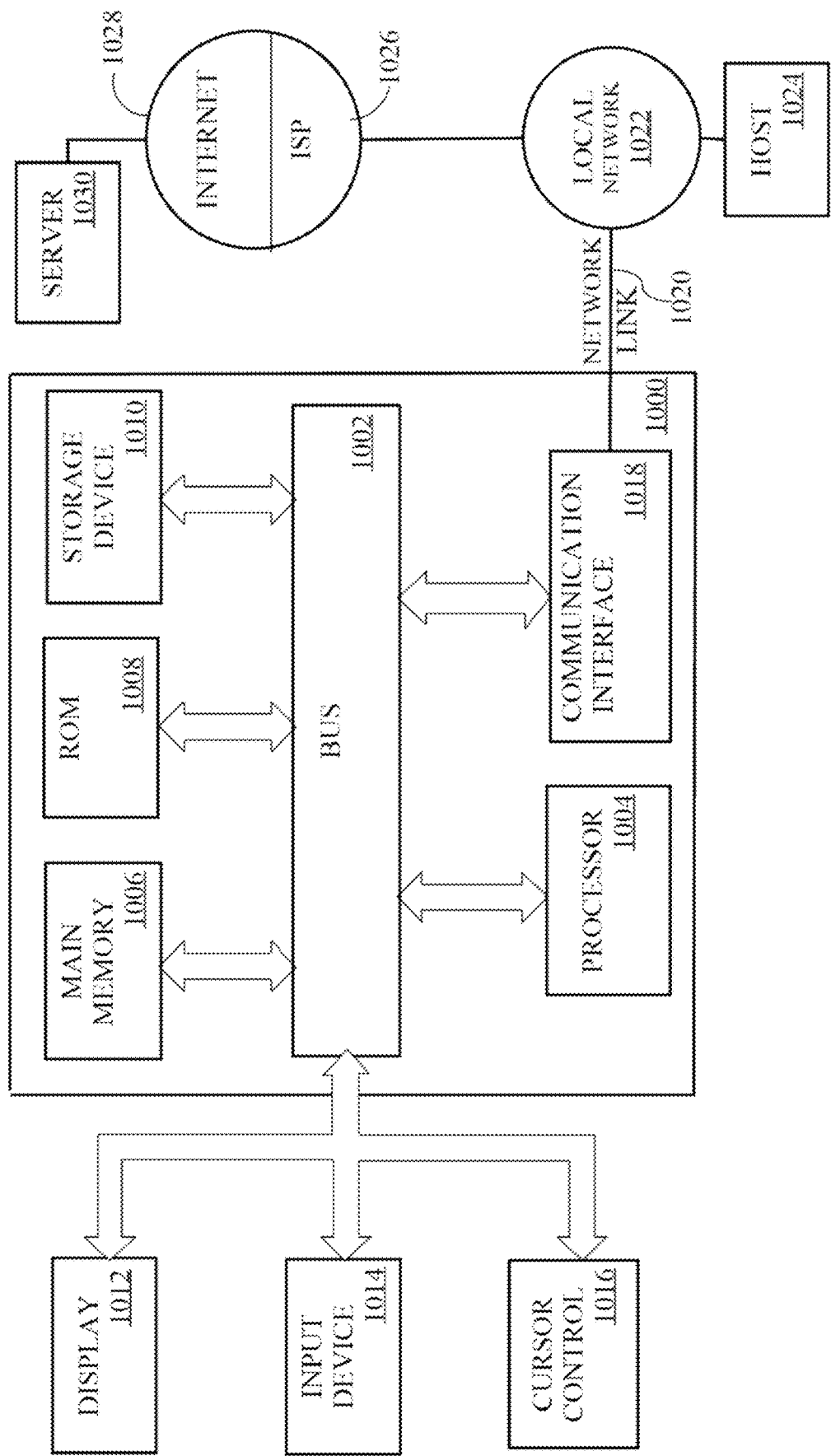
FIG. 10 is a block diagram that illustrates a computer system with which the techniques herein may be implemented.

FIG. 10 is a block diagram that depicts an example computer system 1000 upon which embodiments may be implemented. Computer system 1000 includes a bus 1002 or other communication mechanism for communicating information, and a processor 1004 coupled with bus 1002 for processing information. Computer system 1000 also includes a main memory 1006, such as a random-access memory (RAM) or other dynamic storage device, coupled to bus 1002 for storing information and instructions to be executed by processor 1004. Main memory 1006 also may be used for storing temporary variables or other intermediate information during execution of instructions to be executed by processor 1004. Computer system 1000 further includes a read only memory (ROM) 1008 or other static storage device coupled to bus 1002 for storing static information and instructions for processor 1004. A storage device 1010, such as a magnetic disk or optical disk, is provided and coupled to bus 1002 for storing information and instructions.

Computer system 1000 may be coupled via bus 1002 to a display 1012, such as a cathode ray tube (CRT), for displaying information to a computer user. Although bus 1002 is illustrated as a single bus, bus 1002 may comprise one or more buses. For example, bus 1002 may include without limitation a control bus by which processor 1004 controls other devices within computer system 1000, an address bus by which processor 1004 specifies memory locations of instructions for execution, or any other type of bus for transferring data or signals between components of computer system 1000.

An input device 1014, including alphanumeric and other keys, is coupled to bus 1002 for communicating information and command selections to processor 1004. Another type of user input device is cursor control 1016, such as a mouse, a trackball, or cursor direction keys for communicating direction information and command selections to processor 1004 and for controlling cursor movement on display 1012. This input-device typically has two degrees of freedom in two axes, a first axis (e.g., x) and a second axis (e.g., y), that allows the device to specify positions in a plane.

Computer system 1000 may implement the techniques described herein using customized hard-wired logic, one or more ASICs or FPGAs, firmware and/or program logic or computer software which, in combination with the computer system, causes or programs computer system 1000 to be a special-purpose machine. According to one embodiment, those techniques are performed by computer system 1000 in response to processor 1004 executing one or more sequences of one or more instructions contained in main memory 1006. Such instructions may be read into main memory 1006 from another computer-readable medium, such as storage device 1010. Execution of the sequences of instructions contained in main memory 1006 causes processor 1004 to perform the process steps described herein. In alternative embodiments, hard-wired circuitry may be used in place of or in combination with software instructions to implement the embodiments. Thus, embodiments are not limited to any specific combination of hardware circuitry and software.

The term "computer-readable medium" as used herein refers to any medium that participates in providing data that causes a computer to operate in a specific manner. In an embodiment implemented using computer system 1000, various computer-readable media are involved, for example, in providing instructions to processor 1004 for execution. Such a medium may take many forms, including but not limited to, non-volatile media and volatile media. Non-volatile media includes, for example, optical or magnetic disks, such as storage device 1010. Volatile media includes dynamic memory, such as main memory 1006. Common forms of computer-readable media include, for example, a floppy disk, a flexible disk, hard disk, magnetic tape, or any other magnetic medium, a CD-ROM, any other optical medium, a RAM, a PROM, and EPROM, a FLASH-EPROM, any other memory chip, or memory cartridge, or any other medium from which a computer can read.

Various forms of computer-readable media may be involved in carrying one or more sequences of one or more instructions to processor 1004 for execution. For example, the instructions may initially be carried on a magnetic disk of a remote computer. The remote computer can load the instructions into its dynamic memory and send the instructions over a telephone line using a modem. A modem local to computer system 1000 can receive the data on the telephone line and use an infra-red transmitter to convert the data to an infra-red signal. An infra-red detector can receive the data carried in the infra-red signal and appropriate circuitry can place the data on bus 1002. Bus 1002 carries the data to main memory 1006, from which processor 1004 retrieves and executes the instructions. The instructions received by main memory 1006 may optionally be stored on storage device 1010 either before or after execution by processor 1004.

Computer system 1000 also includes a communication interface 1018 coupled to bus 1002. Communication interface 1018 provides a two-way data communication coupling to a network link 1020 that is connected to a local network 1022. For example, communication interface 1018 may be an integrated service digital network (ISDN) card or a modem to provide a data communication connection to a corresponding type of telephone line. As another example, communication interface 1018 may be a local area network (LAN) card to provide a data communication connection to a compatible LAN. Wireless links may also be implemented. In any such implementation, communication interface 1018 sends and receives electrical, electromagnetic, or optical signals that carry digital data streams representing various types of information.

Network link 1020 typically provides data communication through one or more networks to other data devices. For example, network link 1020 may provide a connection through local network 1022 to a host computer 1024 or to data equipment operated by an Internet Service Provider (ISP) 1026. ISP 1026 in turn provides data communication services through the world-wide packet data communication network now commonly referred to as the "Internet" 1028. Local network 1022 and Internet 1028 both use electrical, electromagnetic, or optical signals that carry digital data streams.

Computer system 1000 can send messages and receive data, including program code, through the network(s), network link 1020 and communication interface 1018. In the Internet example, a server 1030 might transmit a requested code for an application program through Internet 1028, ISP 1026, local network 1022 and communication interface 1018. The received code may be executed by processor 1004 as it is received, and/or stored in storage device 1010, or other non-volatile storage for later execution.

In the foregoing specification, embodiments have been described with reference to numerous specific details that may vary from implementation to implementation. Thus, the sole and exclusive indicator of what is, and is intended by the applicants to be, the approach is the set of claims that issue from this application, in the specific form in which such claims issue, including any subsequent correction. Hence, no limitation, element, property, feature, advantage or attribute that is not expressly recited in a claim should limit the scope of such claim in any way. The specification and drawings are, accordingly, to be regarded in an illustrative rather than a restrictive sense.

What is claimed is:

1. A method for assisting in placements of joint replacement implants during a surgery, the method comprising:
   receiving, by a pinless navigation system, electronic signals carrying data collected by sensors;
   wherein the sensors are pinless, are configured to be placed on a patient's skin without any pins and without skin-penetrating objects, and generate the data by probing a plurality of locations within the patient's body;
   based on, at least in part, the data included in the electronic signals received from the sensors, calculating, by the pinless navigation system and for performing a surgery on the patient, angular and distance values of angular and distance relations between the plurality of locations within the body.

2. The method of claim 1, wherein the sensors are placed on bony prominences on the patient's body;
wherein placing the sensors on the skin does not include protruding or puncturing the patient's skin;
wherein the plurality of locations includes any one of: posterior sacrum, bilateral medial and lateral femoral epicondyles, medial and lateral malleoli, a mid-portion of a patellae or a tibial tubercle;
wherein the angular and distance values comprise any one of: femoral component anteversion and a coronal alignment, changes in a leg length, or changes in a hip offset;
wherein the angular and distance values are displayed on a display device communicatively coupled to the pinless navigation system.

3. The method of claim 1, wherein the sensors comprise an accelerometer and a gyroscope;
wherein a sensor of the sensors is configured to wirelessly transmit the data, collected by the accelerometer and the gyroscope of the sensor, to the pinless navigation system;
wherein the data is transmitted via a wireless protocol that the pinless navigation system implements.

4. The method of claim 1, wherein the pinless navigation system comprises a primary unit;
wherein the primary unit comprises a primary accelerometer and a primary gyroscope;
wherein the primary unit acts as a central processing unit of the pinless navigation system;
wherein the primary unit is a clip-on universally attachable unit that is attached to an implant inserter positioning device;
wherein the primary unit includes an arm that facilitates a universal attachment to any acetabular or femoral component inserter;
wherein the arm has a clip fastener at a terminal end of the arm to assist with a universal attachment to any acetabular or femoral component inserter;
wherein the primary unit acts as a position sensor for a femoral acetabular implant position;
wherein the primary unit is configured to perform any one of: providing a surgeon with real time component position data via a display monitor or providing positioning information for a component positioning via an embedded accelerometer and/or gyroscope unit.

5. The method of claim 4, wherein the primary unit receives, from an intra-incisional greater trochanter sensor, trochanter data collected prior to a femoral neck cut for a total hip arthroplasty to determine an offset of a native hip joint;
wherein the intra-incisional greater trochanter sensor is placed on a greater trochanter and remains in place while trial/final components are utilized to help a surgeon to quantify changes in the offset relative to a preoperative native femoral offset;
wherein the intra-incisional greater trochanter sensor is used to provide trochanter data for calculating a leg length.

6. The method of claim 5, wherein the intra-incisional greater trochanter sensor is a replica of any of the sensors but has a button/clip/fastener that allows the intra-incisional greater trochanter sensor to be fixed to a small diameter metal tack/pin/screw that is placed on the intra-incisional greater trochanter sensor.

7. The method of claim 1, wherein the surgery is any of:
accurate and precise intraoperative positioning of a hip replacement implant or assisting in bony cuts or reaming of bone in a human patient with standalone navigation or robotic assisted joint replacement via a pinless skin based position input sensors;
an accurate and precise intraoperative positioning of a knee replacement implant and/or assisting in bony cuts or reaming of bone in a human patient with standalone navigation or robotic assisted joint replacement via novel pinless wireless or wired skin based position input sensors; or
an accurate and precise intraoperative positioning of a shoulder replacement implant and/or assisting in bony cuts or reaming of bone in a human patient with standalone navigation or robotic assisted joint replacement via novel pinless wireless or wired skin based position input sensors.

8. A pinless navigation system for assisting in precise and accurate placements of joint replacement implants during a surgery, the pinless navigation system comprising:
a primary unit; and
sensors communicatively coupled to the primary unit;
wherein the primary unit:
receives electronic signals carrying data collected by the sensors; wherein the sensors are pinless, are configured to be placed on a patient's skin without any pins and without skin-penetrating objects, and generate the data by probing a plurality of locations within the patient's body;
based on, at least in part, the data included in the electronic signals received from the sensors, calculates, for performing a surgery on the patient, angular and distance values of angular and distance relations between the plurality of locations within the body.

9. The pinless navigation system of claim 8, wherein the sensors are placed on bony prominences on the patient' body;
wherein placing the sensors on the skin does not include protruding or puncturing the patient's skin;
wherein the plurality of locations includes any one of: posterior sacrum, bilateral medial and lateral femoral epicondyles, medial and lateral malleoli, a mid-portion of a patellae or a tibial tubercle;
wherein the angular and distance values comprise any one of: femoral component anteversion and a coronal alignment, changes in a leg length, or changes in a hip offset;
wherein the angular and distance values are displayed on a display device communicatively coupled to the pinless navigation system.

10. The pinless navigation system of claim 8, wherein the sensors comprise an accelerometer and a gyroscope;
wherein a sensor of the sensors is configured to wirelessly transmit the data, collected by the accelerometer and the gyroscope of the sensor, to the pinless navigation system;
wherein the data is transmitted via a wireless protocol that the pinless navigation system implements.

11. The pinless navigation system of claim 8, wherein the pinless navigation system comprises a primary unit;
wherein the primary unit comprises a primary accelerometer and a primary gyroscope;
wherein the primary unit acts as a central processing unit of the pinless navigation system;
wherein the primary unit is a clip-on universally attachable unit that is attached to an implant inserter positioning device;
wherein the primary unit includes an arm that facilitates a universal attachment to any acetabular or femoral component inserter;

wherein the arm has a clip fastener at a terminal end of the arm to assist with a universal attachment to any acetabular or femoral component inserter;

wherein the primary unit acts as a position sensor for a femoral acetabular implant position;

wherein the primary unit is configured to perform any one of: providing a surgeon with real time component position data via a display monitor or providing positioning information for a component positioning via an embedded accelerometer and/or gyroscope unit.

12. The pinless navigation system of claim 11, wherein the primary unit receives, from an intra-incisional greater trochanter sensor, trochanter data collected prior to a femoral neck cut for a total hip arthroplasty to determine an offset of a native hip joint;

wherein the intra-incisional greater trochanter sensor is placed on a greater trochanter and remains in place while trial/final components are utilized to help a surgeon to quantify changes in the offset relative to a preoperative native femoral offset;

wherein the intra-incisional greater trochanter sensor is used to provide trochanter data for calculating a leg length.

13. The pinless navigation system of claim 12, wherein the intra-incisional greater trochanter sensor is a replica of any of the sensors but has a button/clip/fastener that allows the intra-incisional greater trochanter sensor to be fixed to a small diameter metal tack/pin/screw that is placed on the intra-incisional greater trochanter sensor.

14. The pinless navigation system of claim 8, wherein the surgery is any of:

accurate and precise intraoperative positioning of a hip replacement implant or assisting in bony cuts or reaming of bone in a human patient with standalone navigation or robotic assisted joint replacement via a pinless skin based position input sensors;

an accurate and precise intraoperative positioning of a knee replacement implant and/or assisting in bony cuts or reaming of bone in a human patient with standalone navigation or robotic assisted joint replacement via novel pinless wireless or wired skin based position input sensors; or an accurate and precise intraoperative positioning of a shoulder replacement implant and/or assisting in bony cuts or reaming of bone in a human patient with standalone navigation or robotic assisted joint replacement via novel pinless wireless or wired skin based position input sensors.

15. A computer-readable storage medium storing one or more program instructions which, when executed by one or more computer processors, cause the one or more computer processors to perform:

receiving, by a pinless navigation system, electronic signals carrying data collected by sensors;

wherein the sensors are pinless, are configured to be placed on a patient's skin without any pins and without skin-penetrating objects, and generate the data by probing a plurality of locations within the patient's body;

based on, at least in part, the data included in the electronic signals received from the sensors, calculating, by the pinless navigation system and for performing a surgery on the patient, angular and distance values of angular and distance relations between the plurality of locations within the body.

16. The computer-readable storage medium of claim 15, wherein the sensors are placed on bony prominences on the patient's body;

wherein placing the sensors on the skin does not include protruding or puncturing the patient's skin;

wherein the plurality of locations includes any one of: posterior sacrum, bilateral medial and lateral femoral epicondyles, medial and lateral malleoli, a mid-portion of a patellae or a tibial tubercle;

wherein the angular and distance values comprise any one of: femoral component anteversion and a coronal alignment, changes in a leg length, or changes in a hip offset;

wherein the angular and distance values are displayed on a display device communicatively coupled to the pinless navigation system.

17. The computer-readable storage medium of claim 15, wherein the sensors comprise an accelerometer and a gyroscope;

wherein a sensor of the sensors is configured to wirelessly transmit the data, collected by the accelerometer and the gyroscope of the sensor, to the pinless navigation system;

wherein the data is transmitted via a wireless protocol that the pinless navigation system implements.

18. The computer-readable storage medium of claim 15, wherein the pinless navigation system comprises a primary unit;

wherein the primary unit comprises a primary accelerometer and a primary gyroscope;

wherein the primary unit acts as a central processing unit of the pinless navigation system;

wherein the primary unit is a clip-on universally attachable unit that is attached to an implant inserter positioning device;

wherein the primary unit includes an arm that facilitates a universal attachment to any acetabular or femoral component inserter;

wherein the arm has a clip fastener at a terminal end of the arm to assist with a universal attachment to any acetabular or femoral component inserter;

wherein the primary unit acts as a position sensor for a femoral acetabular implant position;

wherein the primary unit is configured to perform any one of: providing a surgeon with real time component position data via a display monitor or providing positioning information for a component positioning via an embedded accelerometer and/or gyroscope unit.

19. The computer-readable storage medium of claim 18, wherein the primary unit receives, from an intra-incisional greater trochanter sensor, trochanter data collected prior to a femoral neck cut for a total hip arthroplasty to determine an offset of a native hip joint;

wherein the intra-incisional greater trochanter sensor is placed on a greater trochanter and remains in place while trial/final components are utilized to help a surgeon to quantify changes in the offset relative to a preoperative native femoral offset;

wherein the intra-incisional greater trochanter sensor is used to provide trochanter data for calculating a leg length.

20. The computer-readable storage medium of claim 19, wherein the intra-incisional greater trochanter sensor is a replica of any of the sensors but has a button/clip/fastener that allows the intra-incisional greater trochanter sensor to be fixed to a small diameter metal tack/pin/screw that is placed on the intra-incisional greater trochanter sensor.

* * * * *

UNITED STATES PATENT AND TRADEMARK OFFICE
CERTIFICATE OF CORRECTION

| | | |
|---|---|---|
| PATENT NO. | : 12,383,342 B2 | Page 1 of 1 |
| APPLICATION NO. | : 17/945483 | |
| DATED | : August 12, 2025 | |
| INVENTOR(S) | : Madhusudhan Reddy Yakkanti and Marshall P. Allegra | |

It is certified that error appears in the above-identified patent and that said Letters Patent is hereby corrected as shown below:

On the Title Page

Item (74) should read:
Attorney, Agent, or Firm -- Patterson & Sheridan, LLP.
                      Malgorzata A. Kulczycka Signed and Sealed this
Fourth Day of November, 2025

John A. Squires
*Director of the United States Patent and Trademark Office*